United States Patent [19]

Palmer et al.

[11] Patent Number: 5,849,790
[45] Date of Patent: Dec. 15, 1998

[54] (MONO) ETHYLENEDIAMIONENITROPLATINUM (IV) COMPLEXES WITH LIGANDS OF OXIDES OF NITROGEN AS POSSIBLE ANTI-TUMOR AGENTS

[75] Inventors: Jay W. Palmer, Tampa; Joseph A. Stanko, Temple Terrace; Saïd M. Sebti, Tampa, all of Fla.; Julia R. Burdge, Barberton, Ohio

[73] Assignee: The University of South Florida, Tampa, Fla.

[21] Appl. No.: 749,264

[22] Filed: Nov. 15, 1996

Related U.S. Application Data

[60] Provisional application No. 60/006,944 Nov. 17, 1994.
[51] Int. Cl.$^6$ ............................ A01N 55/02; A61K 31/28
[52] U.S. Cl. ............................................ 514/492; 556/137
[58] Field of Search ............................... 514/492; 556/137

[56] References Cited

U.S. PATENT DOCUMENTS 5,434,256   7/1995   Khokhar et al. ..................... 556/137

OTHER PUBLICATIONS

Kukushkin et al, Zh. Neorg. Khim. vol. 32 p. 3118 (abst. only), 1987.
Peloso Gazz. Chim. Ital. vol. 110 p. 279 (abst. only), 1980.
Zheligovskaya et al, Zh. Neorg. Khim. vol. 13 p. 822 (abst. only), 1968.
"Oxidation of Platinum (II) Ethylenediamine Complexes with the Oxodes of Nitrogen, NO and $NO_2$; A Model for Synthesis of Platinum (IV) Nitro Compounds as Potential Antitumor Agents"; Julia R. Burdge; Thesis; Aug. 1990.
"Oxidation of Platinum (II) BIS (Ethylenediamine) Complexes with the Oxides of Nitrogen, NO and $No_2$; A Model for Synthesis of Platinum (IV) Nitro Compounds as Potential Antitumor Agents"; Julia R. Burdge, Joseph A. Stanko, Jay W. Palmer; *Florida Scientist*; vol. 58; p. 274.
"Platinum Compounds: A New Class of Potent Anti–Tumor Agents"; Barnett Rosenberg, Loretta VanCamp, James E. Trosko and Virginia Mansour; *Nature*; vol. 222; Apr. 26, 1969; pp. 385–386.

"Rationale for Development of Platinum Analogs"; Joseph H. Burchenal, Kathleen Kalaher, Kimberly Dew and Linda Lokys; *Cancer Treatment Reports*; vol. 63, No. 9–10; Sep./Oct. 1979; pp. 1493–1498.
"The Surprising Life of Nitric Oxide"; Paul L. Feldman, Owen W. Griffith and Dennis G. Stuehr; *C&EN*; Dec. 20, 1993; pp. 26–38.
"Nitric Oxide in Cells"; Jack R. Lancaster, Jr.; *American Scientist*; vol. 80; May/Jun. 1992; pp. 248–259.
"Oxidation of Platinum (II) Mono (ethylenediamine) complexes with the Oxides of Nitrogen, NO and $NO_2$; Possible Anti–Tumor Agents (II)"; Jay W. Palmer, Julia R. Burdge and Joseph A. Stanko; *Florida Scientist*; vol. 58 No. 4; 1995; pp. 359–364.
"Absorption Spectra of Dichloro–(ethylenediamine) Compounds of Platinum (IV)"; I.I. Chernyaev, N.N. Zheligovskaya, and Lieh T'i–k'eng; *Russian Journal of Inorganic Chemistry*; vol. 9 No. 3; Mar. 1964; pp 315–319.
"Nitrosyl Compounds of Platinum and the Reaction of Platinum(II) Compounds with Nitric Acid"; L.A. Nazarova, I.I. Chernyaev, and A.N. Kolesnikova; *Russian Journal of Inorganic Chemistry*; vol. 10 No. 12; Dec. 1965; pp. 1533–1535.
"Dinitro (ethylenediamine) Derivatives of Platinum (IV)"; N.N. Zheligovskaya, I.I. Chernyaev (deceased), and N.P. Vasil'eva; *Russian Journal of Inorganic Chemistry*; vol. 13 No. 3; 1968; pp. 432–434.
"Absorption Spectra of Dinitro (Ethylenediamine) Complexes of Platinum(V)"; I.I. Chernyaev (deceased), N.N. Zheligovskaya, and N.P. Vasil'eva; *Russian Journal of Inorganic Chemistry*; vol. 13 No, 4; 1968; pp. 547–548.
"Nitrosation of Amines in Co–ordination Complexes"; I.I. Chernyaev, O.N. Adrianova, and N.Sh. Leites; *Russian Journal of Inorganic Chemistry*; vol. 6 No. 2; Feb. 1961; pp. 252–253.
"Platin Teil D"; *Gmelins Handbuch Der Anorganischen Chemie* ; vol. 68; 1957; pp. XLVII and 570–573.

*Primary Examiner*—Sheela Huff
*Attorney, Agent, or Firm*—Stein, Schifino & Van Der Wall

[57] ABSTRACT

The present invention discloses (mono) ethylenediaminenitroplatinum (IV) complexes of with ligands of oxides of nitrogen, and their synthesis, which, in vivo, may be reduced to produce "cisplatin" type platinum (II) antitumor complex and nitric oxide, which also reportedly has anti-tumor activity.

12 Claims, 2 Drawing Sheets

(MONO) ETHYLENEDIAMIONENITROPLATINUM (IV) COMPLEXES WITH LIGANDS OF OXIDES OF NITROGEN AS POSSIBLE ANTI-TUMOR AGENTS

REFERENCE TO RELATED APPLICATIONS

This application claims the benefit of U.S. Provisional Application No. 60/006,944 filed Nov. 17, 1995.

FIELD OF THE INVENTION

This invention concerns (mono) ethylenediaminenitroplatinum (IV) complexes with the oxides of nitrogen, and their synthesis.

BACKGROUND

In recent years, an increasing number of people are developing cancer (please see Davis, D. and Hoel, D. (eds.), 1990. *Trends in Cancer Mortality in Industrial Countries.* Ann. N. Y. Acad. Sci. 609, pp. 5–48). As a result, there is an interest in the development of new types of cancer drugs Cisdiaminedichloroplatinum(II) or "Cisplatin" was the first of a class of platinum coordination compounds to be recognized for its antitumor activity (please see Rosenberg, B., Vancamp, L., Trosko, J., and Mansour, v. H. 1969 *Platinum Compounds: A new class of potent antitumor agents*, Nature (London) 222:385–386, incorporated by reference herein and attached hereto as Appendix A). However, even though Cisplatin is effective against a wide variety of human tumors, its high toxicity and low solubility make its administration more difficult (Burchenal, J. H, Kalaher, K., Dew, K., and Lokys, L. 1979. *Rationale for development of platinum Analogs* Cancer Treatment Reports, 63:1493–1498, incorporated by reference herein and attached hereto as Appendix B). Recent research efforts have been made to address these drawbacks. For example, U.S. Pat. No. 5,434,256 discloses 1,4 and 1,2-diaminocyclohexane platinum(IV) complexes that the patentees believe exhibit a greater cytotoxicity towards cancer cells and yet do not exhibit the nephrotoxicity previous observed in heretofore known cis Platinum(II) compounds.

Other non-platinum compounds have also been shown to have a cytotoxic activity. For example, it has been shown that macrophages in the body produce nitric oxide (NO) in amounts sufficient to kill or inhibit the proliferation of tumor cells (please see Feldman, P. L., Griffith, O. W., Stuehr, D. J. 1993. *The surprising life of Nitric Oxide*, Chem. and Eng. News, December 20, incorporated by reference herein and attached hereto as Appendix C). It appears that nitric oxide attacks cancer cells by bonding to the metal enzymes that are involved in their respiration, which prevents them from functioning. The cells actually starve to death (please see Lancaster, J. R., Jr. 1992. *Nitric Oxide in Cells*, Am. Scient., 80:248–259, incorporated by reference herein and attached hereto as Appendix D).

Based upon the above referenced information, applicants performed research to synthesize (mono) ethylenediaminenitroplatinum(IV) complexes which may undergo in vivo reduction in the human body to produce "Cisplatin" type compounds and produce nitric oxide in sufficient quantities for a double attack on tumor cells. The results of their research demonstrated that the bisethylenediamineplatinum(II) complex, [Pten$_2$]$^{2+}$, can be oxidized by nitrogen oxide gases (NO$_2$/H$_2$O and NO/HNO$_3$) to produce bis(ethylenediamine) platinum(IV) complexes containing nitro and nitrito ligands (Burdge, J. R., Stanko, J. A., and Palmer, J. W. 1995. *Oxidation of platinum(II) ethylenediamine complexes with the oxides of nitrogen, NO and NO$_2$: a model of platinum(IV) nitro compounds as potential antitumor agents*, Florida Scient. 58:274–284, incorporated by reference herein and attached hereto as Appendix E). Subsequently, applicants have synthesized similar compounds using the monoethylenediamineplatinum(II) chloride complex [PtenCl$_2$] as a starting material.

SUMMARY OF THE INVENTION

The present invention discloses the successful synthesis of (mono)ethylenediaminenitroplatinum(IV) complexes by oxidation of the platinum (II) complexes with oxides of nitrogen, which applicants believe may have increased cytotoxic activity against cancer cells, decreased host toxicity, and increased solubility in vivo.

The principal object of the present invention is to combine the reported cytotoxic activity of nitric oxide with the reported cytotoxic activity of platinum complexes to form a platinum(IV) complex wherein one to four of the anionic ligands are a nitrogen oxide moiety. Applicants believe that in vivo, these compounds will be reduced to platinum(II) complexes resembling previously known "cisplatin" type compounds and free NO. In applicants' opinion, the concurrent presence of both a "cisplatin" type compound with known anti-cancer activity, and NO, also known to have anti-cancer activity, will provide the present invention with cytotoxic activity greater than that observed in presently known diamine platinum(II) and platinum(IV) complexes. These and other aspects of the present invention will become further apparent from the following detailed description and accompanying drawings.

BRIEF DESCRIPTION OF THE FIGURES

The Figures contained herein are the proposed chemical structures for the starting material principally used to synthesize examples of the present invention and different examples of the present invention. More specifically.

DETAILED DESCRIPTION OF PREFERRED EMBODIMENTS

The following methods and instruments were used to obtain physical measurements on the examples disclosed above. Infrared spectra were recorded on a Beckman 1100 FT IR spectrometer of the range 4000–400 cm$^{-1}$; while x-ray photoelectron spectra binding energies were obtained on a GCA McPherson ESCA 36 photoelectron spectrometer using Al(K) (E=1486.6 ev) as the x-ray source. Microanalyses of carbon, hydrogen, and nitrogen were done by Desert Analytics, Tucson, Ariz.

The Starting Material—[PtenCl$_2$]

Infrared analysis of the purchased [PtenCl$_2$] revealed the typical spectrum of complexed ethylenediamine with N—H bands at 1565 cm$^{-1}$, 1290 cm$^{-1}$ 80 cm$^{-1}$ and at 770 cm$^{-1}$.

Figure 1:
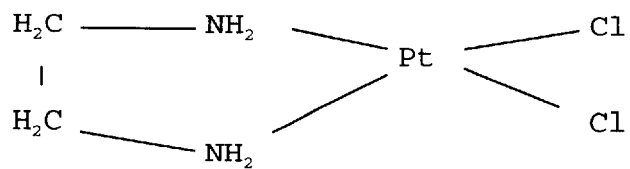
FIG. 1 is the structure of dichloroethylenediamineplatinum(II) [PtenCl$_2$] starting material for the present invention.
Figure 2:
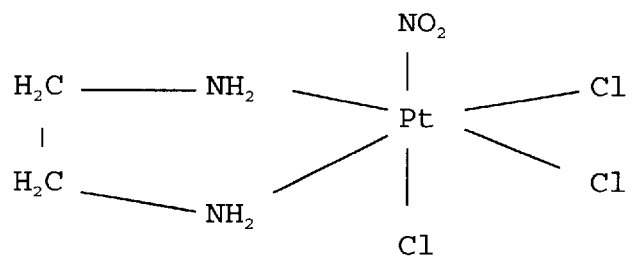
FIG. 2 is the proposed structure of trichloro-nitro-ethylenediamineplatinum(IV) [Pten(NO$_2$)Cl$_3$], one example of the present invention.

Synthesis of [Pten(NO$_2$)Cl$_3$], having a Proposed Structure as Shown in FIG. 2, Using NO$_2$ as Oxidant A mixture of [PtenCl$_2$] (0.3316 dispersed in 25 mL of D.I. water) was magnetically stirred while being treated with NO$_2$ gas for 45 minutes at about the rate of one bubble of gas per second. This gave a blue solution which when concentrated at 50° C. to 3 ml on a hot plate precipitated yellow crystals. The crystals were broken up in 95% ethanol and filtered off to yield 0.1585 g of product (37.8% yield). This infrared spectrum of the product exhibited NO$_2$ bands at 1480 cm$^{-1}$, 1325 cm$^{-1}$, 600 cm$^{-1}$ and an exceeding sharp band at 827 cm$^{-1}$ indicating a coordinated nitro ligand. The N—H rocking mode, present at 770 cm$^{-1}$ in the [PtenCl$_2$] starting material was missing, indicating that the new compound was a platinum(IV) complex. This was confirmed by XPS spectra. Anal: calculated for [Pt(N$_2$C$_2$H$_2$)NO$_2$Cl$_3$] (FW 407.55): C, 5.89; H, 1.98; N, 10.31. Found: C, 5.91; H, 2.03; N, 10.66.

Synthesis of [Pten(NO$_2$)Cl$_3$], Having a Proposed Structure as Shown in FIG. 2, Using NO/HNO$_3$ as Oxidant A solution of [PtenCl$_2$] (0.3166 g dissolved in 20 mL deionized water and 3 mL of 16M nitric acid) was treated with reagent grade NO gas for 7 minutes. During the first 30 seconds, the suspension turned yellow-green which gradually deepened to green and blue-green in 2 minutes. After 7 minutes, no solid remained and color of the solution was deep blue-green; however, after several hours the solution color had faded to yellow. Upon evaporation at room temperature in an air-stream decciator, fine bright yellow crystals of [Pten(NO$_2$)Cl$_3$] were obtained that contained a sharp IR band at 827 cm$^{-1}$, characteristic of an N-coordinated nitro ligand. An N—H rocking band at 770 cm$^{-1}$ was not detected. Anal: calculated for [Pt(N$_2$C$_2$H$_2$)NO$_2$Cl$_3$] (FW 407.55): C, 5.89; H, 1.98; N, 10.31; Cl, 26.10. Found: C, 6.01; H, 1.94; N, 10.07; Cl, 26.87.

Figure 3:
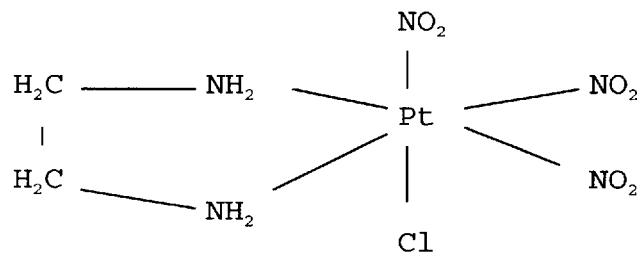
FIG. 3 is the proposed structure of chloro-trinitro-ethylenediamineplatinum(IV) [Pten(NO$_2$)$_3$Cl], another example of the present invention.

Synthesis of [Pten(NO$_2$)$_3$Cl]], Having a Proposed Structure as Shown in FIG. 3, Using NO$_2$ as Oxidant The filtrate obtained in the preparation of [Pten(NO$_2$)Cl$_3$] by using NO$_2$ as an oxidant was evaporated to dryness at 50° C. to remove ethanol and then redissolved in 15 mL H$_2$O. A NO$_2$ gas stream was introduced into the solution (25° C.) for 1 hour at a rate of about 1 bubble per second. The solution became apple green in color and was filtered to give a yellow solution. This filtrate was concentrated on a hot plate at 50° C. to a volume of 1 ml and allowed to stand for three weeks at ambient conditions. A gummy yellowish colored solid, resulted, whose IR spectrum contained a split band at 1480 cm$^{-1}$ and 1455 cm$^{-1}$ as well as an asymmetrical, moderately sharp band at 825 cm$^{-1}$ (broader than [Pten(NO$_2$)Cl$_3$], indicating two types of coordinated nitro (NO$_2$) ligands and a short, broad band at 970 cm$^{-1}$ showing that a small percentage of nitro ligands were present. No N—H rocking mode at 770 cm$^{-1}$ was detected, indicating a Pt(IV) complex. We formulated this complex, II, as predominantly [Pten(NO$_2$)$_3$Cl] based primarily on infrared evidence.

Figure 4:
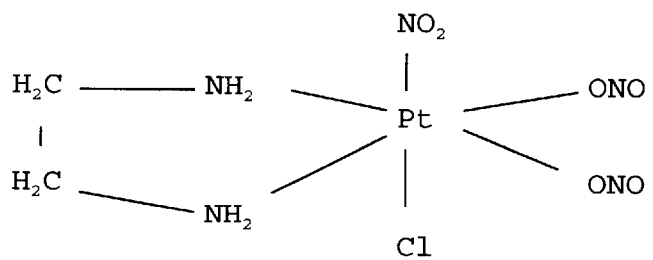
FIG. 4 is the proposed structure of dinitrito-chloro-nitro-ethylenediamineplatinurn(IV) [PtenNO$_2$(ONO)$_2$Cl], yet another example of the present invention

Synthesis of [PtenNO$_2$(ONO)$_2$Cl]], Having a Proposed Structure as Shown in FIG. 4, Using NO/HNO$_3$ as Oxidant A solution of [PtenCl$_2$] (0.9245 g, 2.83 m mole dissolved in 20 mL H$_2$O and 3 ml of 16M HNO$_3$) was treated with a stream of NO gas at a rate of about 1 bubble per second. A green color appeared almost at once which became a deep blue color at 10 minutes. In another 25 minutes, the blue color began dissipating and a small amount of solids began precipitating; therefore, the NO flow as stopped. After standing for three days the solids were removed by filtration, washed and dried in a desiccator giving 0.2649 g of a light yellow product. IR analysis showed the spectrum to be identical to [Pten(NO$_2$)Cl$_3$].

The filtrate (38 mL was allowed to evaporate at ambient conditions to a 10 mL volume and a small amount (0.0148 g) of yellow needles were removed by filtration. The second filtrate (yellow color) was evaporated further using a Rotovac first at 55° C. and then at 73° C. and 6 kPa vacuum to give 0.8337 g of a yellowish-brown material.

The infrared spectrum of this product contained a characteristic sharp band at 827 cm$^{-1}$, indicating coordinated nitro ligands, bands at 1525 cm$^{-1}$, 1280 cm$^{-1}$, and a large broad band at 975 cm$^{-1}$ indicating coordinated nitrito ligands, and a small band at 1720 cm$^{-1}$, suggesting an N=O group. The N—H rocking mode at 770 cm$^{-1}$ characteristic of the [PtenCl$_2$] starting material was not present. Anal: calculated for [PtenNO$_2$(ONO)$_2$Cl] (FW 428.62): C, 5.60; H, 1.87; N, 16.34. Found: C, 5.96; H, 2.00; N, 11.29.

Further drying at 73° C. and 6 kPa vacuum gave a product whose infrared spectrum contained a larger, more asymmetrical nitro band at 825 cm$^{-1}$, a smaller, more asymmetrical nitrito band at 965 cm$^{-1}$, and a much larger, sharp band at 1720 cm$^{-1}$, possibly indicated a N=O group. Analysis found: C, 7.08; H, 2.01; N, 8.98. These analyses indicate continued loss of NO from the product during drying.

Figure 5:
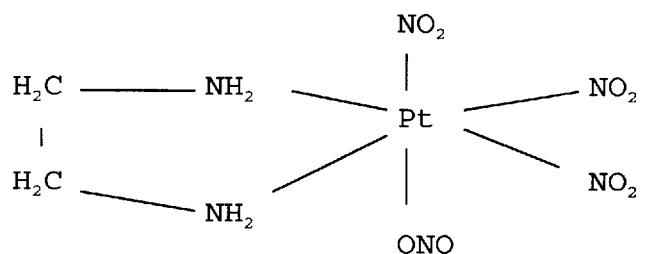
FIG. 5 is the proposed structure of nitrito-trinitro-ehtylenediamineplatinum(IV) [Pten(NO$_2$)$_3$(ONO)], yet another example of the present invention.

Synthesis of [Pten(NO$_2$)$_3$(ONO)]], Having a Proposed Structure as Shown in FIG. 5, Using NO$_2$ as Oxidant A solution of [PtenCl$_2$] 0.3336 g, 1.022×10$^{×3}$ mol dissolved in 15 mL of water) was added to a solution of silver nitrate (0.3478 g, 2.044×10$^{-3}$ mol) to remove the chlorides. The slurry was allowed to react for 6.5 hours at 50° C., and cooled overnight at 10° C. It then was heated to 50° C. and filtered. A 0.2908 g (2.29×10$^{-3}$ mol) amount of silver chloride was obtained.

The filtrate was treated with a NO$_2$ gas stream (about 1 bubble per second) for 45 minutes at 25° C. The solution first turned an intense blue color, which after heating for 4.5 hours at 40° C., was colored yellow, orange and finally brownish, from which solution brown, needle-like crystals appeared. The solution was concentrated to a final volume of 4 mL, cooled to 10° C. and these crystals filtered off yielding 0.1104 g. The infrared spectrum of this product contained a sharp band at 830 cm$^{-1}$ indicating coordinated nitro ligands; however, it also contained a sharp NH band at 777 cm$^{-1}$ indicating a Pt(II) oxidation state that was confirmed by XPS analysis. Anal: calculated for [Pten(NO$_2$)$_2$ (FW 347.39: C, 6.91; H, 2.33; N, 16.13. Found: C, 6.97; H, 2.32; N, 15.74.

The filtrate was concentrated to less than 1 mL at 40° C. and allowed to evaporate to dryness. A yellow, gummy product resulted whose infrared spectrum contained split, moderately sharp bands at 821 cm$^{-1}$ and a shorter one at 839 cm$^{-1}$, indicating two types of coordinated nitro ligands, a broad nitrito band at 970 cm$^{-1}$, and a very small band at 1720 cm$^{-1}$, possibly indicating a N=O group. No NH band was observed at 770 cm$^{-1}$ indicating a platinum(IV) oxidation state. This infrared spectrum suggest a complex with a probable formula of [Pten(NO$_2$)$_3$ONO].

Figure 6:
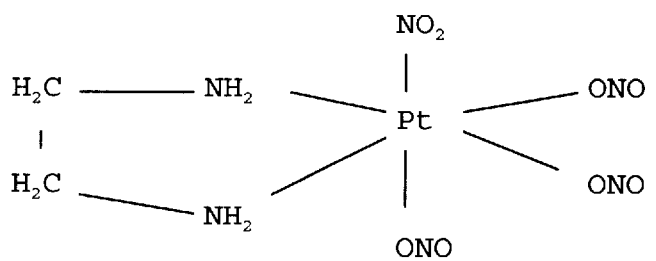
FIG. 6 is the proposed structure trinitrito-nitro-ethylenediamineplatinum(IV) [Pten(NO$_2$)(ONO)$_3$], yet another example of the present invention.

Synthesis of [Pten(NO$_2$)(ONO)$_3$]]Having a Proposed Structure as Shown in FIG. 6, using NO/HNO$_3$ as Oxidant A slurry of diiodoethylenediamineplatinum(II) [PtenI$_2$] (1.2639 g, 2.5×10$^{-3}$ mol dispersed in 60 mL of water) was treated with a solution of AgNO$_3$ (0.8441 g, 5.0×10$^{-3}$ mol) to precipitate the iodide as AgI. The slurry was allowed to react with stirring for 3 hours at 55° C., and cooled overnight at 25° C. and filtered. A 1.1489 g (4.894 mmol) amount of dry silver iodide was obtained.

The filtrate was concentrated at 55° C. to a 30 mL volume and treated with a NO gas stream (about 1 bubble/second) for 45 minutes at 25° C. No color change was noted until 4.5 mL of concentrated nitric acid (16M) was added and the NO gas stream resumed, then it immediately turned a blue color. At the end of the NO addition, the color remained a deep blue which after 4 hours of standing exposed to air, turned green and by the following morning turned pale yellow. The treatment was repeated twice more with NO gas for 15 minutes and the mixture was allowed to stand over night each time.

The solution was then transferred to a Rotovac unit and evaporated to dryness at a maximum temperature of 73° C. and a vacuum reading of 5 kPa to yield 0.9786 g of a brownish product. Its infrared spectrum contained the characteristic sharp nitro band at 827 cm$^{-1}$, and a large asymmetrical, broad nitrito band at 970 cm$^{-1}$. No NH band was present at 7790 cm$^{-1}$ indicating a Pt(IV) oxidation state. Anal: calculated for [PtenNO$_2$(ONO)$_3$] (FW 439.25): C, 5.47; H, 1.84; N, 19.14. Found: C, 5.31; H, 1.69; N, 13.53.

Further drying at 73° C. and 6 kPA gave a product whose infrared spectrum exhibited larger nitro bands at 1495 cm$^{-1}$, 1320 cm$^{-1}$, 480 cm$^{-1}$ and an asymmetrical one at 827 cm$^{-1}$ with a shoulder at 835 cm$^{-1}$, smaller nitrito bands at 1550 cm$^{-1}$, 1280 cm$^{-1}$, 1280 cm$^{-1}$ and 960 cm$^{-1}$ and a much larger band at 1725 cm$^{-1}$, possibly indicating the presence of N=O groups. Anal. found: C, 9.35; H, 2.01; N, 7.90. These analyses indicate continued loss of NO from the product during drying.

Many other variations and modifications of the invention will be apparent to those skilled in the art without departing from the spirit and scope of the invention. The described structures and examples of their syntheses are, therefore, intended to be merely exemplary, and all such variations and modifications are intended to be included within the scope of the invention as defined in the appended claims.

What is claimed is:

1. A (mono)ethylenediaminenitroplatinum (IV) complex having the formula:

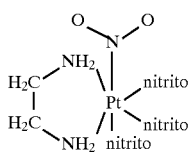

or a stereoisomer thereof.

2. A method for inhibiting the growth of cancer cells in a mammal as described in claim 1, wherein a therapeutically effective amount of the (mono)ethylenediaminenitroplatinum (IV) complex or stereoisomer thereof, is administered to the mammal.

3. A (mono)ethylenediaminenitroplatinum (IV) complex having the formula:

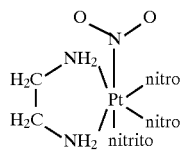

or a stereoisomer thereof.

4. A method for inhibiting the growth of cancer cells in a mammal as described in claim 3, wherein a therapeutically effective amount of the (mono)ethylenediaminenitroplatinum (IV) complex or stereoisomer thereof, is administered to the mammal.

5. A (mono)ethylenediaminenitroplatinum (IV) complex having the formula:

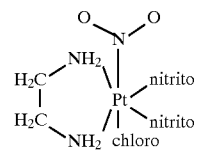

or a stereoisomer thereof.

6. A method for inhibiting the growth of cancer cells in a mammal as described in claim 5, wherein a therapeutically effective amount of the (mono)ethylenediaminenitroplatinum (IV) complex or stereoisomer thereof, is administered to the mammal.

7. A (mono)ethylenediaminenitroplatinum (IV) complex having the formula:

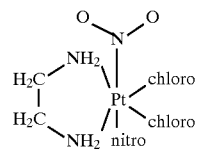

wherein said nitro ligands are trans to one another and said chloro ligands are cis to one another.

8. A method for inhibiting the growth of cancer cells in a mammal as described in claim 7, wherein a therapeutically effective amount of the (mono)ethylenediaminenitroplatinum (IV) complex or stereoisomer thereof, is administered to the mammal.

9. A (mono)ethylenediaminenitroplatinum (IV) complex having the formula:

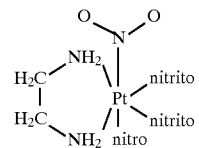

or a stereoisomer thereof.

10. A method for inhibiting the growth of cancer cells in a mammal as described in claim 9, wherein a therapeutically effective amount of the (mono)ethylenediaminenitroplatinum (IV) complex or stereoisomer thereof, is administered to the mammal.

11. A method for inhibiting the growth of cancer cells in a mammal using a (mono)ethylenediaminenitroplatinum (IV) complex having the formula:

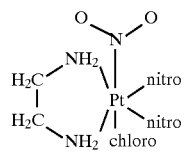

wherein a therapeutically effective amount of the (mono)ethylenediaminenitroplatinum (IV) complex or stereoisomer thereof, is administered to the mammal.

12. A method for inhibiting the growth of cancer cells in a mammal using a (mono)ethylenediaminenitroplatinum (IV) complex having the formula:

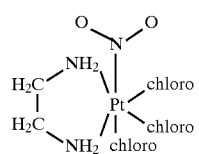
or a stereoisomer thereof;
wherein a therapeutically effective amount of the (mono) ethylenediaminenitroplatinum (IV) complex or stereoisomer thereof, is administered to the mammal.
* * * * *

UNITED STATES PATENT AND TRADEMARK OFFICE
CERTIFICATE OF CORRECTION

PATENT NO : 5,849,790
DATED : Dec. 15, 1998
INVENTOR(S) : Jay W. Palmer; Joseph A. Stanko; Said M. Sebti; Julia R. Burdge It is certified that error appears in the above-identified patent and that said Letters Patent is hereby corrected as shown below:

On the title page, section [60], replace "1994" with --1995--.

Col. 1, Line 18, after "drugs" insert --.--.

Col. 4, Line 33, replace "1.022x10$^{x3}$" with --1.022x10$^{-3}$--.

Signed and Sealed this

Eleventh Day of May, 1999

Q. TODD DICKINSON

*Attest:*

*Attesting Officer*   *Acting Commissioner of Patents and Trademarks*